United States Patent [19]

Fischli et al.

[11] Patent Number: 4,950,677
[45] Date of Patent: Aug. 21, 1990

[54] BENZIMIDAZOLE DERIVATIVE COMPOUNDS AND METHOD OF MAKING

[75] Inventors: Albert Fischli, Riehen; Anna Krasso, Basel; André Szente, Riehen, all of Switzerland

[73] Assignee: Hoffmann-La Roche Inc., Nutley, N.J.

[21] Appl. No.: 222,593

[22] Filed: Jul. 21, 1988

[30] Foreign Application Priority Data

Jul. 29, 1987 [CH] Switzerland ............ 2906/87

[51] Int. Cl.$^5$ ............ C07D 401/04; A61K 31/44
[52] U.S. Cl. ............ 514/338; 514/318; 546/271; 546/193; 540/597
[58] Field of Search ............ 546/271, 193; 514/338, 514/318; 540/597

[56] References Cited

U.S. PATENT DOCUMENTS 4,689,331 8/1987 Ankner et al. ............ 546/271
4,766,133 8/1988 Fischli et al. ............ 546/271

FOREIGN PATENT DOCUMENTS 0181846 5/1986 European Pat. Off. .
1476568 3/1967 France .

OTHER PUBLICATIONS

Derwent No. 86-132721/21 corresponds to U.S. Pat. No. 4,689,331.

Journal of Medicinal Chemistry, vol. 29, 1327–1329 (1986).

Primary Examiner—Jane T. Fan
Attorney, Agent, or Firm—George M. Gould; Bernard S. Leon; A. Kate Huffman

[57] ABSTRACT

A compound of the formula

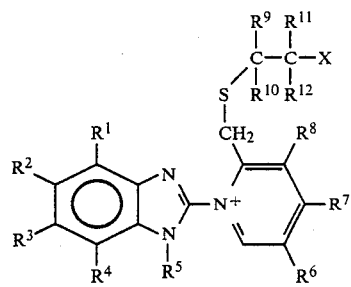

wherein $R^1$–$R^{19}$ are as described in the specification.

The present invention is concerned with benzimidazole derivatives, particularly benzimidazole-2-yl pyridinium compounds of formula I which are pharmaceutically useful in treating or preventing gastric and duodenal ulcers. The invention includes the compounds I, pharmaceutical compositions containing such compounds and the use of such compounds in therapeutic treatment or prevention of gastric and duodenal ulcers.

27 Claims, No Drawings

1 …

BENZIMIDAZOLE DERIVATIVE COMPOUNDS AND METHOD OF MAKING

BACKGROUND OF THE INVENTION

The invention is concerned with benzimidazole derivatives and, in particular, it is concerned with benzimidazol-2-yl pyridinium compounds useful as pharmaceuticals in treating or preventing gastric and duodenal ulcers.

SUMMARY OF THE INVENTION

The present invention is concerned with benzimidazole derivatives, particularly benzimidazol-2-yl pyridinium compounds of formula I hereinbelow, useful as pharmaceuticals in treating or preventing gastric and duodenal ulcers.

These compounds are novel and it has been found that they possess valuable pharmacodynamic properties, namely gastric acid secretion-inhibiting and/or mucosa-protective properties (especially against indomethacin-induced lesions), so that they can be used for the control or prevention of illnesses of the gastrointestinal tract, especially against gastric ulcers and duodenal ulcers.

The present invention includes the compounds themselves as defined above, as well as pharmaceutical compositions containing such compounds, and the us of such compositions in therapeutic treatment or prevention of gastric and duodenal ulcers.

DETAILED DESCRIPTION OF THE INVENTION

The invention is concerned with benzimidazole derivatives. In particular, it is concerned with benzimidazol-2-yl pyridinium compounds of the formula wherein $R^1$, $R^2$, $R^3$ and $R^4$ each are hydrogen, fluorine, chlorine, trifluoromethyl, cyano or a residue of the formula $$-COOR^{13}, -CONR^{14}R^{15}, -SOR^{16} \text{ or } -SO_2R^{16}$$

(a)    (b)    (c)    (d)

or two of $R^1$, $R^2$, $R^3$ and $R^4$, which are adjacent, together with the carbon atoms to which they are attached are a 5-, 6- or 7-membered ring containing at least one of the structural elements $$-CO-, -COO-, -CON(R^{14})-, -SO- \text{ or } -SO_2-,$$

(f)    (g)    (h)    (i)    (j)

with the proviso that of the symbols $R^1$, $R^2$, $R^3$ and $R^4$ at least one and a maximum of three is/are hydrogen;

$R^5$ is hydrogen or a negative charge;

$R^6$ and $R^8$ each are hydrogen or lower alkyl;

$R^7$ is lower alkoxy;

$R^9$ and $R^{10}$ each are hydrogen or lower alkyl and $R^{11}$ and $R^{12}$ each are lower alkyl; or two of the substituents $R^9$ and $R^{10}$ or $R^9$ and $R^{11}$ or $R^{11}$ and $R^{12}$ together with the carbon atom(s) to which they are attached are a 5-, 6- or 7-membered carbocyclic ring and the remaining two of the substituents $R^9$, $R^{10}$, $R^{11}$ and $R^{12}$ each are hydrogen or lower alkyl; or $R^9$ and X together are an additional carbon-carbon bond, $R^{10}$ is hydrogen or lower alkyl and $R^{11}$ and $R^{12}$ each are lower alkyl;

$R^{13}$ is lower alkyl;

$R^{14}$ and $R^{15}$ each are hydrogen or lower alkyl or together with the nitrogen atom are a 5-, 6- or 7-membered saturated heterocyclic ring;

$R^{16}$ is lower alkyl;

X is chlorine, bromine or a residue of the formula $-OR^{17}$ or, as stated above, X and $R^9$ together are an additional carbon-carbon bond;

$R^{17}$ is hydrogen, acyl or a residue of the formula $$-CH(R^{18})R^{19};$$  (k)

$R^{18}$ is hydrogen or lower alkyl; and $R^{19}$ is hydrogen, lower alkyl, lower alkenyl, lower hydroxyalkyl, lower alkoxy-lower-alkyl, hydroxy-lower-alkoxy-lower-alkyl, lower alkoxy-lower-alkoxy-lower alkyl, hydroxy-lower-alkoxy-lower-alkoxy-lower-alkyl, lower alkoxy-lower-alkoxy-lower-alkoxy-lower-alkyl, hydroxy-lower-alkoxy-lower-alkoxy-lower-alkoxy-lower-alkyl, acyloxy-lower-alkyl or acyloxy-lower-alkoxy-lower-alkyl; whereby the molecule as a whole is non-charged or has a single positive charge and whereby in the latter case an external anion is present.

When the molecule as a whole is non-charged, then the benzimidazol-2-yl pyridinium compounds of formula I are present in the form of internal salts. This is the case when $R^5$ is a negative charge.

The term "lower" denotes residues or compounds of from 1 to 7, preferably 1 to 4, carbon atoms.

The term "alkyl" denotes straight-chain or branched saturated hydrocarbon residues such as methyl, ethyl, n-propyl, i-propyl, sec-butyl, t-butyl and the like.

The term "alkoxy" denotes alkyl groups as defined above attached via an oxygen atom.

The term "acyl" denotes residues which are derived from organic acids, especially carboxylic acids, by elimination of the hydroxy group, and it primarily embraces lower alkanoyl residues such as acetyl, propionyl and the like.

The 5-, 6- or 7-membered ring which may be formed with two adjacent substituents $R^1$, $R^2$, $R^3$ and $R^4$ and the carbon atoms to which they are attached may be heterocyclic or carbocyclic, it can optionally contain one or more additional double bonds, in which case the ring can be aromatic or non-aromatic, and it can be substituted or unsubstituted. Substituents which may be used include lower alkyl, especially methyl, oxo or the like. For example, $R^1$ and $R^2$ or $R^2$ and $R^3$ or $R^3$ and $R^4$, taken together, can be a divalent radical of the formula

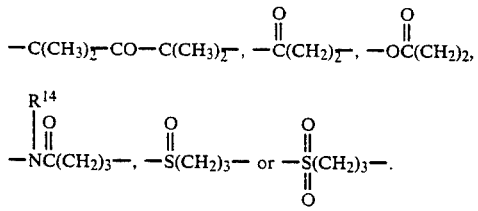

The 5-, 6- or 7-membered ring which may be formed with $R^9$ and $R^{10}$ or $R^9$ and $R^{11}$ or $R^{11}$ and $R^{12}$ and the carbon atom(s) to which they are attached is carbocyclic. For example, $R^9$ and $R^{10}$ or $R^9$ and $R^{11}$ or $R^{11}$ and $R^{12}$, taken together, can be a divalent radical of the formula $-(CH_2)_4-$ or $-(CH_2)_5-$.

The 5-, 6- or 6-membered ring which may be formed with $R^{14}$ and $R^{15}$ and the nitrogen atom to which they are attached is saturated. Examples of such preferred rings include pyrrolidine and piperidine.

The term "external anion" denotes a separated molecule or atom bearing a negative charge.

The term "noncharged" when describing the compounds of the invention denotes that the molecule bears in addition to the compulsory positive charge a negative charge as well.

The term "negative charge" when describing the compounds denotes that there are free electrons in the molecule to the extent that there is one unit of an electric charge is resulting.

The term "intramolecularly" means within the same molecule.

The term "deprotonized" means without a proton.

Conveniently, $R^1$ and $R^4$ each are hydrogen and either $R^2$ and $R^3$ each are fluorine or each are chlorine or together are a residue of the formula $-C(CH_3)_2-CO-C(CH_3)_2-$ or $R^2$ is fluorine or trifluoromethyl and $R^3$ is hydrogen. Preferably, $R^2$ is trifluoromethyl and $R^1$, $R^3$ and $R^4$ each are hydrogen.

Furthermore, conveniently $R^6$ is hydrogen or methyl, $R^7$ is methoxy or ethoxy and $R^8$ is methyl. Methoxy is preferred for $R^7$.

Finally, conveniently either $R^9$ and $R^{10}$ each are hydrogen, $R^{11}$ and $R^{12}$ each are methyl and X is chlorine, hydroxy, methoxy, ethoxy, propoxy, butoxy, acetoxy, 2-hydroxyethoxy, 2-methoxyethoxy, 2-(2-hydroxyethoxy)ethoxy, 2-(2-methoxyethoxy)ethoxy, 2-[2-(2-hydroxyethoxy)ethoxy]ethoxy or 2-[2-(2-methoxyethoxy)ethoxy]ethoxy; or $R^9$ and X together are an additional carbon-carbon bond, $R^{10}$ is hydrogen and $R^{11}$ and $R^{12}$ each are methyl; or $R^9$ and $R^{11}$ together are tetramethylene, $R^{10}$ and $R^{12}$ each are hydrogen and X is methoxy. Preferably, $R^9$ and $R^{10}$ each are hydrogen, $R^{11}$ and $R^{12}$ each are methyl and X is chlorine, hydroxy, methoxy, ethoxy, propoxy, acetoxy, 2-hydroxyethoxy or 2-methoxyethoxy; or $R^9$ and X together are an additional carbon-carbon bond, $R^{10}$ is hydrogen and $R^{11}$ and $R^{12}$ each are methyl. In an especially preferred embodiment, $R^9$ and $R^{10}$ each are hydrogen, $R^{11}$ and $R^{12}$ each are methyl and X is ethoxy, acetoxy, 2-hydroxyethoxy or 2-methoxyethoxy.

A particularly preferred compound of formula I is:

2-[[[2-(2-Hydroxyethoxy)-2-methylpropyl]thio]methyl]-4-methoxy-3-methyl-1-[5-(trifluoromethyl)-2-benzimidazolyl]pyridinium methanesulfonate.

Especially preferred compounds of formula I are:

Intramolecularly deprotonized 2-[[[2-(2-hydroxyethoxy)-2-methylpropyl]thio]methyl]-4-methoxy-3-methyl-1-[-5-(trifluoromethyl)-2-benzimidazolyl]-pyridinium cation;

4-methoxy-2-[[[2-(2-methoxyethoxy)-2-methylpropyl]thio]methyl]-3-methyl-1-[5-(trifluoromethyl)-2-benzimidazolyl]pyridinium methanesulfonate;

Intramolecularly deprotonized 4-methoxy-2-[[[2-(2-methoxyethoxy)-2-methylpropyl]thio]methyl]-3-methyl-1-[5-(trifluoromethyl)-2-benzimidazolyl]pyridinium cation;

2-[[(2-acetoxy-2-methylpropyl)thio]methyl]-4-methoxy-3-methyl-1-[5-(trifluoromethyl)-2-benzimidazolyl]pyridinium methanesulfonate;

2-[[(2-acetoxy-2-methylpropyl)thio]methyl]-4-methoxy-3-methyl-1-[5-(trifluoromethyl)-2-benzimidazolyl]pyridinium chloride;

Intramolecularly deprotonized 2-[[(2-acetoxy-2-methylpropyl)thio]methyl]-4-methoxy-3-methyl-1-[5-(trifluoromethyl)-2-benzimidazolyl]pyridinium cation;

2-[[(2-ethoxy-2-methylpropyl)thio]methyl]-4-methoxy-3-methyl-1-[5-(trifluoromethyl) 2-benzimidazolyl]pyridinium methanesulfonate;

2-[[(2-ethoxy-2-methylpropyl)thio]methyl]-4-methoxy-3-methyl-1-[5-(trifluoromethyl)-2-benzimidazolyl]pyridinium chloride; and Intramolecularly deprotonized 2-[[(2-ethoxy-2-methylpropyl)thio]methyl]-4-methoxy-3-methyl-1-[5-(trifluoromethyl)-2-benzimidazolyl]pyridinium cation.

Likewise preferred compounds of formula I are, for example;

Intramolecularly deprotonized 2-[[(2-chloro-2-methylpropyl)thio]methyl]-4-methoxy-3-methyl-1-[5-(trifluoro-methyl)-2-benzimidazolyl]pyridinium cation;

2-[[(2-chloro-2-methylpropyl)thio]methyl]-4-methoxy-3-methyl-1-[5-(trifluoromethyl)-2-benzimidazolyl]pyridinium chloride;

Intramolecularly deprotonized 2-[[(2-hydroxy 2-methylpropyl)thio]methyl]-4-methoxy-3-methyl-1-[5-(trifluoromethyl)-2-benzimidazolyl]pyridinium cation;

Intramolecularly deprotonized 4-methoxy-2-[[(2-methoxy-2-methylpropyl)thio]methyl]-3-methyl-1-[5-(trifluoromethyl)-2-benzimidazolyl]pyridinium cation;

Intramolecularly deprotonized 4-methoxy-3-methyl-2-[[(2-methylpropenyl)thio]methyl]-1-[5-(trifluoromethyl)2-benzimidazolyl]pyridinium cation;

Intramolecularly deprotonized 4-methoxy-3-methyl-2-[[(2-methyl-2-propoxypropyl)thio]methyl]-1-[5-(trifluoromethyl)-2-benzimidazolyl]pyridinium cation;

4-methoxy-3-methyl-2-[[(2-methylpropenyl)thio]methyl]1-[5-(trifluoromethyl)-2-benzimidazolyl]-pyridinium chloride; and Intramolecularly deprotonized 2-[[(2-hydroxy-2-methylpropyl)thio]methyl]-4-methoxy-3,5-dimethyl-1-[5-(trifluoromethyl)-2-benzimidazolyl]pyridinium cation.

The compounds of formula I can be prepared by (a) reacting a compound of the formula

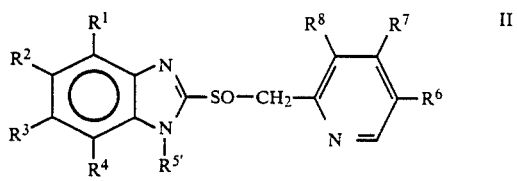

wherein $R^1$, $R^2$, $R^3$, $R^4$, $R^6$, $R^7$ and $R^8$ are as defined above and $R^{5'}$ is hydrogen, under acidic conditions with a compound of the formula

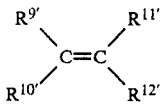

III wherein $R^{9'}$ and $R^{10'}$ each are hydrogen or lower alkyl and $R^{11'}$ and $R^{12'}$ each are lower alkyl or two of the substituents $R^{9'}$ and $R^{10'}$ or $R^{9'}$ and $R^{11'}$ or $R^{11'}$ and $R^{12'}$ together with the carbon atom(s) to which they are attached are a 5-, 6- or 7-membered carbocyclic ring and two of the remaining substituents $R^{9'} R^{10'}$, $R^{11'}$ and $R^{12'}$ each are hydrogen or lower alkyl,
and a compound of the formula

HX'    IV wherein X' is chlorine, bromine or a residue of the formula —$OR^{17}$ and $R^{17}$ is hydrogen or a residue of formula (k) above;
(b) reacting a compound of formula I in which X is chlorine or bromine with a compound of the formula

HOR$^{17'}$    V wherein $R^{17'}$ is hydrogen or a residue of formula (k) above; or
(c) dehydrating a compound of formula I in which X is a residue of the formula $OR^{17}$ and $R^{17}$ is hydrogen; or
(d) acylating a compound of formula I in which X is a residue of the formula —$OR^{17}$, $R^{17}$ is hydrogen or a residue of formula (k) above and $R^{19}$ is lower hydroxyalkyl or hydroxy lower alkoxy-lower alkyl;
whereupon the product obtained is isolated as a salt or internal salt and, if desired, an internal salt is converted into a pharmaceutically acceptable salt.

Compounds of formula I in which either $R^9$ and $R^{10}$ each are hydrogen or lower alkyl and $R^{11}$ and $R^{12}$ each are lower alkyl or ln which two of the substituents $R^9$ and $R^{10}$ or $R^9$ and $R^{11}$ or $R^{11}$ and $R^{12}$ together with the carbon atom(s) to which they are attached are a 5-, 6- or 7-membered carbocyclic ring and two of the remaining substituents $R^9$, $R^{10}$, $R^{11}$ and $R^{12}$ each are hydrogen or lower alkyl and in which X is chlorine, bromine or a residue of the formula —$OR^{17}$ and $R^{17}$ is hydrogen or a residue of formula (k) are obtained in accordance with process aspect (a). Compounds such as isobutylene, cyclohexene or the like are used as components of formula III and hydrogen chloride, hydrogen bromide, water or an alcohol of the formula

HO—CH($R^{18}$)$R^{19}$    VI wherein $R^{18}$ and $R^{19}$ have the significance mentioned earlier, are used as components of formula IV.

When hydrogen chloride or hydrogen bromide is used as the component of formula IV, then a corresponding compound of formula I in which X is chlorine or bromide is obtained. In this case, the starting material of formula II is reacted with hydrogen chloride or hydrogen bromide in the presence of the corresponding component of formula III, conveniently in t-butanol, in which case it can be advantageous to add a small amount of molecular sieve. The hydrogen chloride or hydrogen bromide used as the component of formula IV thereby simultaneously serves to bring about the required acidic conditions. Under certain circumstances the component of formula III need not be used as such. When, for example, in the end product of formula I $R^9$ and $R^{10}$ each are hydrogen, $R^{11}$ and $R^{12}$ each are methyl and X is chlorine or bromine, then a corresponding compound of formula II can be reacted in t-butanol with hydrogen chloride or hydrogen bromide. In such a case the corresponding component of formula III, i.e. isobutylene, is formed in situ from the t-butanol under the action of the hydrogen chloride or hydrogen bromide. The reaction is preferably effected at about room temperature and, depending on the remaining reaction parameters, takes about a half hour to about four days.

When water is used as the component of formula IV, then a corresponding compound of formula I in which X is hydroxy is obtained. In accordance with this embodiment, the components of formulas II and III are reacted with one another under acidic-aqueous conditions, for example, in aqueous hydrochloric acid, aqueous methanesulfonic acid or the like. It can be advantageous to add a water-miscible organic solvent which is inert under the reaction conditions such as, for example, tetrahydrofuran or the like.

When an alcohol of formula VI above is used as the component of formula IV, then a corresponding compound of formula I in which X is a residue of the formula —$OR^{17}$ and $R^{17}$ is a residue of formula (k) above is obtained. The alcohol of formula VI used as the component of formula IV can simultaneously also serve as the solvent. Methanesulfonic acid, hexafluorophosphoric acid, tetrafluoroboric acid or the like is conveniently used as the acid. The reaction is conveniently effected at room temperature and, depending on the remaining reaction parameters, takes about 20 minutes to about 20 hours.

Process aspect (b) yields compounds of formula I in which either $R^9$ and $R^{10}$ each are hydrogen or lower alkyl and $R^{11}$ and $R^{12}$ are lower alkyl or two of the substituents $R^9$ and or $R^9$ and $R^{11}$ or $R^{11}$ and $R^{12}$ together with the carbon atom(s) to which they are attached are a 5-, 6- or 7-membered carbocyclic ring and the remaining two of substituents $R^9$, $R^{10}$, $R^{11}$ and $R^{12}$ each are hydrogen or lower alkyl and in which X is a residue of the formula —$OR^{17}$ and $R^{17}$ is a residue of formula (k). Water or an alcohol of formula VI is used as the component of formula V. The reaction is conveniently effected under acidic conditions, i.e. the starting material of formula I in which X is chlorine or bromine is reacted with aqueous acid (e.g. dilute hydrochloric acid) or with a solution of an acid such as methanesulfonic acid or the like in the corresponding alcohol of formula VI. It can be advantageous to add an organic solvent which is inert under the reaction conditions and which is miscible with water or the alcohol of formula VI. The reaction is effected at about room temperature which is about 23° C. and, depending on the remaining reaction parameters, takes a few (e.g., about 5 to 15) hours.

Process aspect (c) yields compounds of formula I in which $R^9$ and X together are an additional carbon-carbon bond, $R^{10}$ is hydrogen or lower alkyl and $R^{11}$ and $R^{12}$ each are lower alkyl. The dehydration in accordance with this process aspect is effected according to suitable methods which are known to persons skilled in the art. Polyphosphoric acid ethyl ester, polyphosphoric acid or the like is used as the dehydrating agent. The dehydration is conveniently carried out in an organic medium which is inert under the reaction conditions, for example, in a halogenated hydrocarbon such as chloroform, 1,2-dichloroethane, an aromatic hydrocarbon such as toluene, benzene, or the like, or in a mixture of two or more of such solvents such as chloroform/toluene. The reaction is conveniently effected at the reflux temperature and, depending on the remaining reaction parameters, takes several (e.g. about 2 to 3) days.

Process aspect (d) yields compounds of formula I in which $R^9$ and $R^{10}$ each are hydrogen or lower alkyl, $R^{11}$ and $R^{12}$ each are lower alkyl and X is a residue of the formula $-OR^{17}$ in which $R^{17}$ is acyl or a residue of formula (k), wherein $R^{19}$ is acyloxy-lower-alkyl or acyloxy-lower-alkoxy-lower alkyl. The acylation is effected according to suitable methods which are generally known to those persons skilled in the art, advantageously by means of a reactive derivative of the acid corresponding to the acyl residue to be introduced, for example, by means of an acid anhydride, an acid halide, etc. The introduction of an acetyl group can be effected by reacting the starting material of formula I in acetic acid with acetic anhydride. It can be of advantage to add a small amount of perchloric acid, toluenesulfonic acid or the like. The acylation is conveniently effected at about room temperature and, depending on the remaining reaction parameters, takes a few (e.g., 4 to 6) hours.

Depending on the nature of the starting materials and on the reaction conditions which are used the products obtained can be isolated as salts or as internal salts. If desired, internal salts can be converted into pharmaceutically acceptable salts, for example with hydrogen chloride, hydrogen bromide, phosphoric acid, sulfuric acid, citric acid, methanesulfonic acid, p-toluene-sulfonic acid and the like.

The starting materials of formula II are known or can be prepared readily according to suitable methods known in the art. Moreover, some of the Examples further below contain detailed information concerning the preparation of certain compounds of formula II.

As mentioned earlier, the benzimidazol-2-yl pyridinium compounds of formula I have valuable pharmacodynamic properties.

Representative compounds of formula I were investigated with respect to their anti-ulcer activity, and gastric acid secretion-inhibiting activity. Toxicology studies were also conducted.

The experimental procedure described hereinafter was used to determine the anti-ulcer activity:

A number of groups of 8 male rats each with a body weight of 130–150 g are used for each dosage of a test substance. Prior to the beginning of the experiment the animals receive no food for 24 hours, but receive water ad libitum. Various dosages of the substances to be tested (suspended in 0.5% tragacanth) or the vehicle alone (controls) are administered twice perorally, namely. 1 hour before and 2 hours after the peroral administration 20 mg/kg of indomethacin. In the control animals, this dosage of indomethacin leads to lesions of the stomach within 5 hours. The animals are killed 6 hours after the first administration of the substance under investigation (or of the vehicle alone). The rats which remain protected from the occurrence of macroscopically visible lesions to the mucous membrane of the stomach are counted. The $ED_{50}$ is that dosage of a test substance at which 50% of the animals are protected from the occurence of such lesions.

The experimental procedure described hereinafter was used to determine the gastric acid secretion-inhibiting activity:

A part of the stomach fundus of female and male beagle hounds is separated from the remainder of the stomach in the form of a pouch of the Heidenhain type by a modification of the method described in Rudick et al., J. Surgical Research 7, 383–398 (1967). In the pouch there is fitted a steel cannula which is conducted externally through the abdominal wall. Before each experiment the animals receive no food for 18 hours, but receive water ad libitum. They are conscious and standing during the experiment and their gastric acid secretion is stimulated by the intravenous infusion of 4-methylhistamine, a selective against of the histamine $H_2$-receptors. The gastric acid production is determined in 15 minute fractions of the stomach pouch juice. As soon as the gastric acid production has a constant value, the substances to be tested are administered orally as a dry powder filled into gelatin capsules. The $ED_{50}$ is that dosage of a test substance which brings about a 50% inhibition of the gastric acid production caused by 4-methylhistamine in the treated animals in comparison to the controls.

In the following Table there are given for a series of representative compounds of formula I the results of the testing with respect to their anti-ulcer activity and to their gastric secretion inhibiting activity. Moreover, this Table contains data concerning the acute toxicity ($LD_{50}$ in the case of single oral administration to mice).

| Compound | Anti-ulcer, $ED_{50}$ mg/kg p.o. | Gastric acid secretion-inhibition, $ED_{50}$ mg/kg p.o. | Toxicity LD 50 mg/kg p.o. |
|---|---|---|---|
| A | 4.4 | 4.9 | 2500–5000 |
| B | 6.1 | 3.9 | 2500–5000 |
| C | 6.0 | 5.5 | 1000–2000 |
| D | 7.0 | 4.8 | 2500–5000 |
| E | 3.2 | 3.0 | 2500–5000 |
| F | 1.9 | 1.8 | 1250–2500 |
| G | 2.8 | 1.5 | 2500–5000 |
| H | 3.2 | 4.3 | — |
| I | 4.1 | 3.8 | 2500–5000 |
| J | 4.6 | 3.7 | >5000 |

A = 2-[[[2-(2-Hydroxyethoxy)-2-methylpropyl]thio]methyl]-4-methoxy-3-methyl-1-[5-(trifluoromethyl)-2-benzimidazolyl]pyridinium methanesulfonate;
B = Intramolecularly deprotonized 2-[[[2-(2-hydroxyethoxy)-2-methylpropyl]thio]methyl]-4-methoxy-3-methyl-1-[5-(trifluoromethyl)-2-benzimidazolyl]pyridinium cation;
C = 4-Methoxy-2-[[[2-(2-methoxyethoxy)-2-methylpropyl]thio]methyl]-3-methyl-1-[5-(trifluoromethyl)-2-benzimidazolyl]pyridinium methanesulfonate;
D = Intramolecularly deprotonized 4-methoxy-2-[[[2-(2-methoxyethoxy)-2-methylpropyl]thio]methyl]-3-methyl-1-[5-(trifluoromethyl)-2-benzimidazolyl]pyridinium cation;
E = 2-[[(2-Acetoxy-2-methylpropyl)thio]methyl]-4-methoxy-3-methyl-1-[5-(trifluoromethyl)-2-benzimidazolyl]pyridinium methanesulfonate;
F = 2-[[(2-Acetoxy-2-methylpropyl)thio]methyl]-4-methoxy-3-methyl-1-[5-(trifluoromethyl)-2-benzimidazolyl]pyridinium chloride;
G = Intramolecularly deprotonized 2-[[(2-acetoxy-2-methylpropyl)thio]methyl]-4-methoxy-3-methyl-1-[5-(trifluoromethyl)-2-benzimidazolyl]pyridinium cation;

H=2-[[(2-Ethoxy-2-methylpropyl)thio]methyl]-4-methoxy-3-methyl-1-[5-(trifluoromethyl)-2-benzimidazolyl]pyridinium methanesulfonate;
I=2-[[(2-Ethoxy-2-methylpropyl)thio]methyl]-4-methoxy-3-methyl-1-[5-(trifluoromethyl)-2-benzimidazolyl]pyridinium chloride; and
J=Intramolecularly deprotonized 2-[[(2-ethoxy-2-methylpropyl)thio]methyl]-4-methoxy-3-methyl-1-[5-(trifluoromethyl)-2-benzimidazolyl]pyridinium cation.

The compounds defined above can be used as medicaments, e.g. in the form of pharmaceutical preparations. Oral administration in the form of solid pharmaceutical preparations such as tablets, coated tablets, dragees, hard gelatin capsules and soft gelatin capsules is preferred. Oral administration in the form of liquid pharmaceutical preparations such as solutions, emulsions and suspensions, rectal administration, e.g. in the form of suppositories, or parenteral administration, e.g., in the form of injection solutions, may also be used.

Pharmaceutical preparations or compositions containing one of the compounds defined above are another aspect of the present invention. The preparation of such medicaments can be effected by bringing one or more of the compounds defined above and, if desired, one or more other therapeutically active substances into a galenical administration form together with one or more therapeutically inert excipients.

For the preparation of tablets, coated tablets, dragees and hard gelatin capsules the compounds defined above can be processed with pharmaceutically inert inorganic or organic excipients. Such excipients may include lactose, maize starch or derivatives thereof, talc, stearic acid or its salts, etc, for tablets, dragees and hard gelatin capsules. For the preparation of pharmaceutical preparations which are resistant to gastric fluid it is necessary to apply a gastric fluid-resistant coating which can consist, e.g., of hydroxypropylmethyl-cellulose phthalate.

Soft gelatin capsules may include such suitable excipients as vegetable oils, waxes, fats, semi-solid and liquid polyols or any other suitable materials known in the art.

For the preparation of solutions and syrups, suitable excipients may include water, polyols, saccharose, invert sugar, glucose and the like.

For suppositories, suitable excipients include, e.g., natural or hardened oils, waxes, fats, semi liquid or liquid polyols and the like.

Injection solutions may include suitable excipients such as, e.g., water, alcohols, polyols, glycerine, vegetable oils or any other suitable materials known in the art.

The pharmaceutical preparations may further include preserving agents, solubilizers, stabilizing agents, wetting agents. emulsifying agents, sweetening agents, coloring agents, flavoring agents, salts for varying the osmotic pressure, buffers, coating agents or antioxidants. Other therapeutically valuable substances may also be included in the preparations.

In accordance with the invention the compounds defined above can be used in the control or prevention of illnesses, for example, in the control or prevention of gastric ulcers and duodenal ulcers. The dosage can vary within wide limits and is determined according to individual requirements in each particular case. In general, in the case of oral administration a daily dosage of about 30–400 mg should be appropriate and in the case of intravenous administration a daily dosage of about 30–400 mg should be appropriate.

The use of the compounds defined above for the preparation of pharmaceutical compositions for the treatment or prevention of gastric and duodenal ulcers is still another aspect of the invention.

The following Examples illustrate the present invention but are not intended to limit its extent in any manner. Ohile the examples describe what are at present considered to be the preferred embodiments of this invention, it will be obvious to those skilled in the art that various changes and modifications may be made therein without departing from the invention, and it is, therefore, aimed to cover all such changes and modifications as falling within the true spirit and scope of the invention.

Unless otherwise stated, percentages and ratios relating to solvent mixtures are expressed in volume, and the remaining percentages and ratios are expressed in weight. Temperatures are in degrees Celsius (°C.), normal pressure is about 1 atmosphere, and room temperature is about 23° C. Unless indicated otherwise, the Examples were carried out as written.

EXAMPLE 1

A suspension of 15 g of 2[[(4-methoxy-3-methyl-2-pyridyl)methyl]sulfinyl]-5-(trifluoromethyl)benzimidazole in a solution of 7.2 g of isobutylene in 130 ml of tert.-butanol was treated with 20 g of molecular sieve (Union Carbide, Type 3A) and with a solution of 19.5 g of gaseous hydrogen chloride in 150 ml of tert.-butanol. The reaction mixture was stirred at room temperature for 50 minutes and subsequently poured into a mixture of ice and 1.2 l of aqueous sodium bicarbonate solution, whereupon methylene chloride was added. The insoluble part of the mixture was filtered off over silica gel and the filtrate was extracted several times with methylene chloride. The organic phases were combined, dried with sodium sulfate, filtered and concentrated. The residue was dissolved in 800 ml of methylene chloride, whereupon 28 g of silica gel (particle size: 0.04–0.06 mm) were added and the mixture was stirred at room temperature for one hour. The silica gel was filtered off, the filtrate was concentrated and the residue was crystallized from ether. The intramolecularly deprotonized 2-[[(2-chloro-2-methylpropyl)thio]methyl]-4-methoxy-3-methyl-1-[5-(trifluoromethyl)-2-benzimidazolyl]-pyridinium cation obtained exhibited a melting point of 132°–134° (decomposition).

EXAMPLE 2

100 mg of intramolecularly deprotonized 2-[[(2-chloro-2-methylpropyl)thio]methyl]-4-methoxy-3-methyl-1-[5-(trifluoromethyl)-2-benzimidazolyl]-pyridinium cation were dissolved in 5 ml of ethyl acetate, whereupon 0.5 ml of 4.7N methanolic hydrochloric acid was added, the solution was concentrated and the residue was crystallized from tert.-butyl methyl ether/ether. The 2-[[(2-chloro-2-methylpropyl)thio]methyl]-4-methoxy-3-methyl-1-[5-(trifluoromethyl)-2-benzimidazolyl]pyridinium chloride obtained exhibited a melting point of 140°–142° (decomposition).

EXAMPLE 3

A suspension of 5 g of intramolecularly deprotonized 2-[[(2-chloro-2-methylpropyl)thio]methyl]-4 -methoxy-3-methyl-1-[5-(trifluoromethyl)-2-benzimidazolyl]-pyridinium cation in 100 ml of 1N aqueous hydrochloric acid was stirred at room temperature for nine hours and then poured into a mixture of ice and aqueous sodium bicarbonate solution, whereupon the mixture was extracted several times with methylene chloride. The combined methylene chloride extracts were dried with sodium sulfate, filtered and concentrated. The residue was recrystallized twice from ether, whereby there was obtained intramolecularly deprotonized 2-[[(2-hydroxy-2-methylpropyl)thio]methyl]-4-methoxy-3methyl-1-[5-(trifluoromethyl)-2-benzimidazolyl]pyridinium cation of melting point 144°–145°.

EXAMPLE 4

A solution of 200 mg of methanesulfonic acid and about 1 g of gaseous isobutylene in 20 ml of methanol was treated with 370 mg of 2-[[(4-methoxy-3-methyl-2-pyridyl)methyl]sulfinyl]-5-(trifluoromethyl)benzimidazole, whereupon the reaction mixture was stirred at room temperature for 18 hours and then evaporated. The residue was treated with methylene chloride and aqueous sodium bicarbonate solution, the methylene chloride phase was separated and the aqueous phase was extracted with methylene chloride. The combined organic phases were dried and concentrated. By recrystallization of the residue from ether/n-hexane there was obtained intramolecularly deprotonized 4-methoxy-2-[[(2-methoxy-2-methylpropyl)thio]methyl]-3-methyl-1-[5-(trifluoromethyl) 2 benzimidazolyl]pyridinium cation of melting point 155°–156°.

EXAMPLE 5

A solution of 200 mg of methanesulfonic acid and about 0.5 g of gaseous isobutylene in 20 ml of ethanol was treated with 350 mg of 2-[[(4-methoxy-3-methyl-2-pyridyl)methyl]sulfinyl]-5-(trifluoromethyl)benzimidazole, whereupon the reaction mixture was stirred at room temperature for 18 hours, concentrated and the residue was treated with methylene chloride and aqueous sodium bicarbonate solution. Thereupon, the methylene chloride phase was separated and the aqueous phase was extracted with methylene chloride. The combined organic phases were dried and concentrated. By recrystallization of the residue from ether there was obtained intramolecularly deprotonized 2-[[(2-ethoxy-2-methylpropyl)thio]methyl]-4-methoxy-3-methyl-1-[5-(trifluoromethyl)-2-benzimidazolyl]pyridinium cation of melting point 132°–134°.

EXAMPLE 6

10 ml of ethylene glycol monomethyl ether saturated with isobutylene were treated with 192 mg of methanesulfonic acid and 370 mg of 2-[[(4-methoxy-3-methyl 2-pyridyl)methyl]sulfinyl]-5-(trifluoromethyl)benzimidazole. The solution was stirred at room temperature under an isobutylene atmosphere for four hours and then concentrated. The residue was treated with methylene chloride and aqueous sodium bicarbonate solution, whereupon the methylene chloride phase was separated and the aqueous phase was extracted with methylene chloride. The combined organic phases were dried and concentrated. The residue was crystallized from ether and there was obtained intramolecularly deprotonized 4-methoxy-2-[[[2-(2-methoxyethoxy)-2-methylpropyl]thio]methyl]-3-methyl-1-[5-(trifluoromethyl)-2-benzimidazolyl]pyridinium cation of melting point 110°–112° (decomposition).

EXAMPLE 7

4 ml of ethylene glycol saturated with isobutylene were treated with 200 mg of methanesulfonic acid and 370 mg of 2-[[(4-methoxy-3-methyl-2-pyridyl)methyl]sulfinyl]-5-(trifluoromethyl)benzimidazole. The solution was stirred at room temperature under an isobutylene atmosphere for nine hours and then poured on to ice and sodium bicarbonate. The resulting aqueous solution was extracted several times with methylene chloride. The combined organic phases were dried and evaporated. The residue was chromatographed on silica gel with methylene chloride/methanol (10:1) as the elution agent, with the medium pressure flash chromatography method being used. By recrystallization from ether/n-hexane there was obtained intramolecularly deprotonized 2-[[[2-(2-hydroxyethoxy) -2-methylpropyl]thio]methyl]-4-methoxy-3-methyl-1-[5-(trifluoromethyl)-2-benzimidazolyl]pyridinium cation of melting point 60°–70°.

EXAMPLE 8

(a) 10.6 g of 5-fluoro-2-benzimidazolethiol were suspended in 570 ml of alcohol and treated with 13.1 g of 2-chloromethyl-4-methoxy-3-methylpyridine hydrochloride. A solution of 5 g of sodium hydroxide in 130 ml of water was added dropwise thereto while cooling with ice, the mixture was left to boil at reflux overnight and then concentrated to about ⅓ of the volume in a vacuum. After the addition of 500 ml of water the resulting crystals were filtered off and washed thoroughly firstly with water and then with ether. There was obtained 5-fluoro-2-[[(4-methoxy-3-methyl-2-pyridyl)methyl]thio]benzimidazole of melting point 128°.

(b) 2.0 g of 5-fluoro-2-[[(4-methoxy-3-methyl-2-pyridyl)methyl]thio]benzimidazole dissolved in 100 ml of methylene chloride were treated with 1.2 g of potassium carbonate. 1.6 g of m-chloroperbenzoic acid were added thereto at −30°, the solution was stirred for a further 5 minutes and subsequently poured into a mixture of 30 ml of saturated sodium bicarbonate solution and 30 ml of water. The organic phase was separated, dried over sodium sulfate, treated with 5.0 ml of triethylamine and evaporated in a vacuum. Crystallization of the residue from methylene chloride/petroleum ether (low boiling)/ether gave 5-fluoro-2-[[(4-methoxy-3-methyl-2-pyridyl)methyl]sulfinyl]benzimidazole of melting point 175°.

(c) A solution of 3.2 g of 5-fluoro-2-[[(4-methoxy-3-methyl-2-pyridyl)methyl]sulfinyl]benzimidazole in 200 ml of tert.butanol was saturated with isobutylene gas for 30 minutes, then treated with a freshly prepared solution of 22.4 g of hydrogen chloride gas in 200 ml of tert. butanol, stirred at room temperature overnight and subsequently evaporated in a vacuum. The residue was taken up in methylene chloride, whereupon the solution was extracted with 100 ml of saturated sodium bicarbonate solution, washed neutral with water. dried and concentrated in a vacuum. Crystallization of the residue from methylene chloride/petroleum ether (low-boiling) yielded intramolecularly deprotonized 2-[[(2-chloro-2-methylpropyl)thio]methyl]-1-(5-fluoro-2-benzimidazolyl)-4-methoxy-3-methylpyridinium cation of melting point 136°–138°.

EXAMPLE 9

A solution of 2 g of methanesulfonic acid in 200 ml of methanol was saturated with isobutylene gas for 30 minutes, then treated with 3.2 g of 5-fluoro-2-[[(4-methoxy-3-methyl-2-pyridyl)methyl]sulfinyl]benzimidazole, stirred at room temperature overnight and subsequently evaporated in a vacuum. The residue was taken up in methylene chloride, whereupon the solution was extracted with 100 ml of saturated sodium bicarbonate solution, washed neutral with water, dried and concentrated in a vacuum. Crystallization of the residue from methylene chloride/petroleum ether (low-boiling) gave intramolecularly deprotonized 1-(5-fluoro-2-benzimidazolyl)-4-methoxy-2-[[(2-methoxy-2-methylpropyl)thio]methyl]-3-methylpyridinium cation of melting point 142°–143°.

EXAMPLE 10

450 mg of intramolecularly deprotonized 2-[[(2-ethoxy-2-methylpropyl)thio]methyl]-4-methoxy-3-methyl-1-[5-(trifluoromethyl)-2-benzimidazolyl]-pyridinium cation were dissolved in methylene chloride, whereupon 2 ml of 4.7N methanolic hydrochloric acid were added thereto, the solution was concentrated and the residue was crystallized from ether. The 2-[[(2-ethoxy-2-methylpropyl)thio]methyl]-4-methoxy-3-methyl-1-[5-(trifluoromethyl)-2-benzimidazolyl]-pyridinium chloride obtained exhibited a melting point of 119°–120°.

EXAMPLE 11

370 mg of intramolecularly deprotonized 2-[[[2-(2-hydroxyethoxy)-2-methylpropyl]thio]methyl]-4-methoxy-3-methyl-1-[5-(trifluoromethyl)-2-benzimidazolyl]pyridinium cation were dissolved in methanol, whereupon 100 mg of methanesulfonic acid were added thereto, the solution was concentrated and the residue was crystallized from ether/ethyl acetate. The 2-[[[2-(2-hydroxyethoxy)-2-methylpropyl]thio]methyl]-4-methoxy-3-methyl-1-[5-(trifluoromethyl)-2-benzimidazolyl]pyridinium methanesulfonate obtained exhibited a melting point of 105°–107° (decomposition).

EXAMPLE 12

483.5 mg of intramolecularly deprotonized 4-methoxy-2-[[[2-(2-methoxyethoxy)-2-methylpropyl]thio]methyl]-3-methyl-1-[5-(trifluoromethyl)-2-benzimidazolyl]pyridinium cation were dissolved in 5 ml of methanol, whereupon 96 mg of methanesulfonic acid were added thereto, the solution was concentrated and the residue was dissolved several times in ethyl acetate and the solution was concentrated each time. The resinous residue was dried in a high vacuum, whereby 4-methoxy-2-[[[2-(2-methoxyethoxy)-2-methylpropyl]thio]methyl]-3-methyl-1-[5-(trifluoromethyl)-2-benzimidazolyl]-pyridinium methanesulfonate was obtained as a foam. The microanalysis showed the following values:

Empirical formula; $C_{23}H_{29}F_3N_3O_3S$ 1:1$CH_3SO_3$; MW 579.65

Calc.: C 49.73% H 5.56% N 7.25% S 11.06%
Found: C 49.59% H 5.76% N 7.19% S 10.97%

EXAMPLE 13

A solution of 160 mg of gaseous isobutylene and 350 mg of 2-[[(4-methoxy-3-methyl-2-pyridyl)methyl]sulfinyl]-5-(trifluoromethyl)benzimidazole in 5 ml of diethylene glycol monomethyl ether was treated with 200 mg of methanesulfonic acid, whereupon the reaction mixture was stirred at room temperature for 18 hours and then neutralized with 100 ml of saturated aqueous sodium bicarbonate solution. The sodium bicarbonate solution was extracted several times with ether; the combined organic phases were dried over sodium sulfate and concentrated. The residue was chromatographed on silica gel with methylene chloride/methanol (20:1) as the elution agent, with the medium pressure flash chromatography method being used. By recrystallization from n-hexane there was obtained intramolecularly deprotonized 4-methoxy-2-[[[2-[2-(2-methoxyethoxy)ethoxy]-2-methylpropyl]thio]methyl]-3-methyl-1-[5-(trifluoromethyl)-2-benzimidazolyl]-pyridinium cation of melting point 103°–106°.

EXAMPLE 14

A solution of 500 mg of intramolecularly deprotonized 2-[[(2-hydroxy-2-methylpropyl)thio]methyl]-4-methoxy-3-methyl-1-[5-(trifluoromethyl)-2-benzimidazolyl]pyridinium cation in 1.5 ml of acetic anhydride and 3 ml of acetic anhydride was treated with 3 drops of perchloric acid and stirred at room temperature for 5 hours. The reaction mixture was neutralized with saturated aqueous sodium bicarbonate solution, extracted several times with methylene chloride, the extracts were dried over sodium sulfate, filtered and the methylene chloride was removed by evaporation. The residue was chromatographed on silica gel with methylene chloride/methanol (10:1) as the elution agent, using the medium pressure flash chromatography method. By crystallization from ether/n-hexane there was obtained intramolecularly deprotonized 2-[[(2-acetoxy-2-methylpropyl)thio]methyl]-4-methoxy-3-methyl-1-[5-(trifluoromethyl)-2-benzimidazolyl]pyridinium cation of melting point 71°–78°.

EXAMPLE 15

467.5 mg of intramolecularly deprotonized 2-[[(2-acetoxy-2-methylpropyl)thio]methyl]-4-methoxy-3-methyl-1-[5-(trifluoromethyl)-2-benzimidazolyl]-pyridinium cation were dissolved in 5 ml of methanol, whereupon 96 mg of methanesulfonic acid were added thereto, the solution was concentrated, the residue was dissolved several times in ethyl acetate and the solution was again concentrated each time. The resinous residue was dried in a high vacuum, whereby 2-[[(2-acetoxy-2-methylpropyl)thio]methyl]-4-methoxy-3-methyl-1-[5-(trifluoromethyl)-2-benzimidazolyl]pyridinium methanesulfonate (1:1) was obtained as a foam. The microanalysis showed the following values:

Empirical formula; $C_{22}H_{25}F_3N_3O_3S$ 1:1 $CH_3SO_3$; MW 563.61

Calc.: C 49.02% H 5.01% N 7.46% S 11.38%
Found; C 48.87% H 5.28% N 7.30% S 11.00%

EXAMPLE 16

A solution of 1 g of methanesulfonic acid and about 1 g of gaseous isobutylene in 15 ml of n-propanol was treated with 2 g of 2-[[(4-methoxy-3-methyl-2-pyridyl)methyl]sulfinyl]-5-(trifluoromethyl)benzimidazole, whereupon the mixture was stirred at room temperature for 18 hours in a flask equipped with a cooling trap (acetone/dry-ice) and then evaporated. The residue was treated with methylene chloride and aqueous sodium bicarbonate solution. The methylene chloride phase was separated and the aqueous phase was extracted with methylene chloride. The combined organic phases were dried and concentrated. The residue was chromatographed on silica gel with methylene chloride/methanol (20:1) as the elution agent, using the medium pressure flash chromatography method. By crystallization from ether/n-hexane there was obtained intamolecularly deprotonized 4-methoxy-3-methyl-2-[[(2-methyl-2-propoxypropyl)thio]methyl]-1-[(5-(trifluoromethyl)-2-benzimidazolyl]pyridinium cation of melting point 106°–108°.

EXAMPLE 17

A solution of 2 g of methanesulfonic acid and about 2 g of gaseous isobutylene in 5 ml of diethylene glycol was treated with 3 g of 2-[[(4-methoxy-3-methyl-2-pyridyl)methyl]sulfinyl]-5-(trifluoromethyl)benzimidazole, whereupon the mixture was stirred at room temperature for 18 hours in a flask equipped with a cooling trap (acetone/dry-ice) and then evaporated. The residue was treated with methylene chloride and aqueous sodium bicarbonate solution, the methylene chloride phase was separated and the aqueous phase was extracted with methylene chloride. The combined organic phases were dried and concentrated. The residue was chromatographed on silica gel (particle size: 0.04–0.06 mm) with methylene chloride/methanol (20:1) as the elution agent, using the medium pressure flash chromatography method.

The purified intramolecularly deprotonized 2-[[[2-[2-(2-hydroxyethoxy)ethoxy]-2-methylpropyl]thio]methyl]-4-methoxy-1-[5-(trifluoromethyl)-2-benzimidazolyl]pyridinium cation was dissolved several times in ethyl acetate and the solution obtained was concentrated each time. The resinous residue was dried in a high vacuum, yielding a foam. The microanalysis showed the following values:

Empirical formula; $C_{24}H_{30}F_3N_3O_4S$; MW 513.57
Calc.: C 56.13% H 5.89% N 8.18% S 6.24%
Found: C 55.74% H 6.06% N 8.00% S 6.21%

EXAMPLE 18

A solution of 1 g of methanesulfonic acid and about 1 g of gaseous isobutylene in 15 ml of n-butanol were treated with 2 g of 2-[[(4-methoxy-3-methyl-2-pyridyl)methyl]sulfinyl]-5-(trifluoromethyl)benzimidazole, whereupon the mixture was stirred at room temperature for three hours in a flask equipped with a cooling trap (acetone/dry-ice) and then evaporated. The residue was treated with methylene chloride and aqueous sodium bicarbonate solution, the methylene chloride phase was separated and the aqueous phase was extracted with methylene chloride. The combined organic phases were dried and concentrated. The residue was chromatographed on silica gel with methylene chloride/methanol (20:1) as the elution agent, using the medium pressure flash chromatography method. By crystallization from ether/n-hexane intramolecularly deprotonized 2-[[(2-butoxy-2-methylpropyl)thio]methyl]-4-methoxy-3-methyl-1-[5-(trifluoromethyl)-2-benzimidazolyl]pyridinium cation of melting point 78°–80° was obtained.

EXAMPLE 19

A solution of 19 g of polyphosphoric acid ethyl ester and 6.3 g of intramolecularly deprotonized 2-[[(2-hydroxy-2-methylpropyl)thio]methyl]-4-methoxy-3-methyl-1-[5-(trifluoromethyl)-2-benzimidazolyl]pyridinium cation in 150 ml of chloroform and 45 ml of toluene was heated at reflux for about 60 hours. The reaction mixture was poured into saturated aqueous sodium carbonate solution, extracted several times with methylene chloride, the combined extracts were dried over sodium sulfate and the methylene chloride was removed by evaporation. The residue was chromatographed on silica gel with methylene chloride/methanol (20:1) as the elution agent, using the medium pressure flash chromatography method. By crystallization from ether/n-hexane there was obtained intramolecularly deprotonized 4-methoxy-3-methyl-2-[[(2-methylpropenyl)thio]methyl]-1-[5-(trifluoromethyl)-2-benzimidazolyl]pyridinium cation of melting point 126°–127°.

EXAMPLE 20

60 mg of intramolecularly deprotonized 4-methoxy 3-methyl-2-[[(2-methylpropenyl)thio]methyl]-1-[5-(trifluoromethyl)-2-benzimidazolyl]pyridinium cation were dissolved in methylene chloride, whereupon 0.5 ml of 4.7N methanolic hydrochloric acid was added thereto, the solution was concentrated and the residue was crystallized from ethyl acetate/ether. The 4-methoxy-3-methyl-2-[[(2-methylpropenyl)thio]methyl]-1-[5-(trifluoromethyl)-2-benzimidazolyl]pyridinium chloride obtained exhibited a melting point of 142°–144°.

EXAMPLE 21

A solution of 2 g of methanesulfonic acid in 200 ml of abs. ethanol was saturated with isobutylene gas for 45 minutes and then treated with 3.2 g of 5-fluoro-2-[[(4-methoxy-3-methyl-2-pyridyl)methyl]sulfinyl]benzimidazole, whereupon the mixture was stirred at room temperature overnight and subsequently evaporated in a vacuum. The residue was taken up in methylene chloride, whereupon the solution was extracted with 100 ml of saturated sodium bicarbonate solution washed neutral, dried and concentrated in a vacuum. Chromatography on silica gel with methanol-methylene chloride (5:95) and subsequent crystallization from methylene chloride/petroleum ether (low-boiling) gave intramolecularly deprotonized (-)-2-[[(2-ethoxy-2-methylpropyl)thio]methyl]-1-[(5-fluoro-2-benzimidazolyl)-4-methoxy-3-methylpyridinium cation of melting point 121°–122°.

EXAMPLE 22

A solution of 2 g of methanesulfonic acid in 200 ml of dioxan was saturated with isobutylene gas for 45 minutes and then treated with 3.2 g of 5-fluoro-2-[[(4-methoxy-3-methyl-2-pyridyl)methyl]sulfinyl]benzimidazole. After stirring for 10 minutes, 5 ml of ethylene glycol were added thereto, whereupon the mixture was stirred at room temperature for 48 hours and subsequently evaporated in a vacuum. The residue was taken up in methylene chloride, whereupon the solution was extracted with 100 ml of saturated sodium bicarbonate solution, washed neutral with water, dried and concentrated in a vacuum. Crystallization from methylene chloride/abs. ether/petroleum ether (low-boiling) yielded intramolecularly deprotonized 1-(5-fluoro-2-benzimidazolyl)-2-[[[2-(2-hydroxyethoxy)-2-methylpropyl]thio]methyl]-4-methoxy-3-methylpyridinium cation of melting point 75°–80°.

EXAMPLE 23

(a) 40.7 g of 4,5-difluoro-o-phenylenediamine dihydrochloride were suspended in 655 ml of isopropanol. A solution of 22.5 g of potassium hydroxide in 250 ml of water was added dropwise thereto while stirring and the mixture was treated with 39.7 g of potassium ethyl xanthogenate, whereupon the solution was boiled at reflux overnight, then diluted with 300 ml of water and made neutral with glacial acetic acid. The resulting suspension was stirred at 60°–70° for an additional hour. The isopropanol was largely removed from the mixture in a vacuum. After the addition of 1 liter of water, the solid was filtered off washed with water and then dissolved in ether. The solution was then extracted with 1.2 liters of water, treated with active charcoal, dried and evaporated in a vacuum. The residue was suspended in petroleum ether (low boiling) and filtered off. There was obtained 5,6-difluoro-2-benzimidazolethiol of melting point above 300°.

(b) A suspension of 23 g of 5,6-difluoro-2-benzimidazolethiol in 740 ml of alcohol was treated with 22.1 g of 2-chloromethyl-4-methoxy-3-methylpyridine hydrochloride. A solution of 10 g of sodium hydroxide in 350 ml of water was added dropwise thereto while cooling with ice, the mixture was left to boil at reflux overnight and then concentrated to about ⅓ of its volume in a vacuum. After the addition of 1200 ml of water the crystals were filtered off and thereupon washed thoroughly first with water and then with ether. There was obtained 5,6-difluoro-2-[[(4-methoxy-3-methyl-2-pyridyl)methyl]thio]benzimidazole of melting point 216°–218°.

(c) A solution of 13.7 g of 5,6-difluoro-2-[[(4-methoxy 3-methyl-2-pyridyl)methyl]thio]benzimidazole in 800 ml of methylene chloride and 130 ml of methanol was treated with 6.9 g of potassium carbonate. 9.6 g of m-chloroperbenzoic acid were added thereto at −30°, whereupon the solution was stirred for a further 5 minutes and subsequently poured into a mixture of 200 ml of saturated sodium bicarbonate solution and 200 ml of water. The separated organic phase was dried over sodium sulfate, treated with 5.0 ml of triethylamine and evaporated in a vacuum. Crystallization from methylene chloride-methanol-ether yielded 5,6-difluoro-2-[[(4-methoxy-3-methyl-2-pyridyl))methyl]sulfinyl]benzimidazole of melting point 188°–189°.

(d) A solution of 2 g of methanesulfonic acid in 200 ml of methanol was saturated with isobutylene gas for 45 minutes and then treated with 3.37 g of 5,6-difluoro-2-[[(4-methoxy-3-methyl-2 pyridyl)methyl]sulfinyl]benzimidazole, whereupon the mixture was stirred at room temperature overnight and subsequently evaporated in a vacuum. The residue was taken up in methylene chloride, whereupon the solution was extracted with 100 ml of saturated sodium bicarbonate solution, washed neutral with water, dried and concentrated in a vacuum. Crystallization of the residue from methylene chloride/petroleum ether (low boiling) gave intramolecularly deprotonized 1-(5,6-difluoro-2-benzimidazolyl)-4-methoxy-2-[[(2-methoxy-2-methylpropyl)thio]methyl]-3-methylpyridinium cation of melting point 153°–155°.

EXAMPLE 24

A solution of 2 g of methanesulfonic acid in 200 ml of ethanol was saturated with isobutylene gas for 45 minutes, then treated with 3.37 g of 5,6-difluoro-2-[[(4-methoxy-3-methyl-2-pyridyl))methyl]sulfinyl]benzimidazole, stirred at room temperature overnight and subsequently evaporated in a vacuum. The residue was taken up in methylene chloride, whereupon the solution was extracted with 100 ml of saturated sodium bicarbonate solution, washed neutral with water, dried and concentrated in a vacuum. Crystallization of the residue from methylene chloride/petroleum ether (low-boiling) gives intramolecularly deprotonized 1-(5,6-difluoro-2-benzimidazolyl)-4-methoxy-2-[[(2-ethoxy-2-methylpropyl)thio]methyl]-3-methylpyridinium cation of melting point 122°–124°.

EXAMPLE 25

A solution of 3.37 g of 5,6-difluoro-2-[[(4-methoxy-3-methyl-2-pyridyl))methyl]sulfinyl]benzimidazole in 200 ml of tert. butanol was saturated with isobutylene gas for 45 minutes, then treated with a freshly prepared solution of 23 g of hydrogen chloride gas in 200 ml of tert. butanol, stirred at room temperature for 48 hours and subsequently evaporated in a vacuum. The residue was taken up in methylene chloride, whereupon the solution was extracted with 100 ml of saturated sodium bicarbonate solution, washed neutral with water, dried and concentrated in a vacuum. Crystallization of the residue from methylene chloride/petroleum ether (low-boiling) gave intramolecularly deprotonized 2-[[(2-chloro-2-methylpropyl)thio]methyl]-1-(5,6-difluoro-2-benzimidazolyl]4-methoxy-3-methylpyridinium cation of melting point 138°–140°.

EXAMPLE 26

500 mg of 5,7-dihydro-2-[[(4-methoxy-3-methyl-2-pyridyl)methyl]sulfinyl]-5,5,7,7-tetramethylindeno[5,6-d]imidazol-6(1H)-one were dissolved in 50 ml of tert.-butanol saturated with gaseous hydrochloric acid and left to stand at room temperature for 3 days. The reaction mixture was concentrated and the residue was crystallized from ethyl acetate. The 2-[[(2-chloro-2-methylpropyl)thio]methyl]-4-methoxy-3-methyl-1-(1,5,6,7-tetrahydro-5,5,7, 7-tetramethyl- 6-oxoindeno[5,6-d]imidazol-2-yl)-pyridinium chloride obtained exhibited a melting point of 168°–172° (decomposition).

EXAMPLE 27

A suspension of 1.75 g of 2-[[(4-methoxy-3-methyl-2-pyridyl)methyl]sulfinyl]-5-(trifluoromethyl)benzimidazole in a solution of 800 mg of isobutylene in 25 ml of triethylene glycol monomethyl ether was treated with 1 g of methanesulfonic acid and stirred at room temperature for 18 hours. The reaction mixture was neutralized with saturated aqueous sodium bicarbonate solution; the aqueous phase was extracted several times with ether and the combined organic phases were dried over sodium sulfate and concentrated. The residue was chromatographed on silica gel with ether and methylene chloride/methanol (20:1) as the elution agent, using the medium pressure flash chromatography method. The resinous reaction product was dried in a high vacuum, whereby intramolecularly deprotonized 4-methoxy-2-[[[2-(2-methoxyethoxy)ethoxy]ethoxy]-2-methylpropyl]thio]methyl]-3-methyl-1-[5-(trifluoromethyl)-2-benzimidazolyl]pyridinium cation was obtained as a foam. The microanalysis showed the following values:

Empirical formula; $C_{27}H_{36}F_3N_3O_5S$; MW 571.66
Calc.: C 56.73% H 6.35% N 7.35% S 5.61%
Found: C 56.30% H 6.19% N 7.39% S 5.77%

EXAMPLE 28

A suspension of 1.75 g of 2-[[(4-methoxy-3-methyl-2-pyridyl)methyl]sulfinyl]-5-(trifluoromethyl)benzimidazole in 25 ml of triethylene glycol was treated under an isobutylene atmosphere with 1 g of methanesulfonic acid and stirred at room temperature for 25 minutes. The reaction mixture was neutralized with saturated aqueous sodium bicarbonate solution; the aqueous phase was extracted several times with ethyl acetate and the combined organic phases were dried over sodium sulfate and concentrated. The residue was chromatographed on silica gel with ether/methylene chloride (20:1) and methylene chloride/methanol (20:1) as the elution agent, using the medium pressure flash chromatography method. The resinous reaction product was dried in a high vacuum, whereby intramolecularly deprotonized 2-[[[2-[2-[2-(2-hydroxyethoxy)ethoxy]ethoxy]-2-methylpropyl]thio]methyl]-4-methoxy-3-methyl-1-[5-(trifluoromethyl)-2-benzimidazolyl]-pyridinium cation was obtained as a foam. The microanalysis showed the following values:

Empirical formula; $C_{26}H_{34}F_3N_3O_5S \cdot 8H_2O \cdot O0.25$ AcOEt MW 594.07
Calc.: C 54.59% H 6.38% N 7.07% S 5.40%
Found: C 54.75% H 6.57% N 7.00% S 5.52%

EXAMPLE 29

A suspension of 1.75 g of 2-[[(4-methoxy-3-methyl-2-pyridyl)methyl]sulfinyl]-5-(trifluoromethyl)benzimidazole in 25 ml of tetraethylene glycol was treated under a constant isobutylene atmosphere with 1 g of methanesulfonic acid and stirred at room temperature for 25 minutes. The reaction mixture was neutralized with saturated aqueous sodium bicarbonate solution. The aqueous phase was extracted several times with ethyl acetate and the combined organic phases were dried over sodium sulfate and concentrated. The residue was chromatographed on silica gel with ether/methylene chloride (20:1) and methylene chloride/methanol (20:1) as the elution agent, using the medium pressure flash chromatography method. The resinous reaction product was dried in a high vacuum, whereby intramolecularly deprotonized 2-[[[2-[2-[2-[2-(2-hydroxyethoxy)ethoxy]ethoxy]ethoxy]-2-methylpropyl]thio]methyl]-4-methoxy-3-methyl-1-[5-(trifluoromethyl)-2-benzimidazolyl]pyridinium cation was obtained as a foam. The microanalysis showed the following values:

Empirical formula; $C_{28}H_{38}F_3N_3O_6S$; MW 601.68
Calc.: C 55.89% H 6.37% N 6.98% S 5.33%
Found: C 55.25% H 6.67% N 6.43% S 5.06%

EXAMPLE 30

A solution of 62 mg of gaseous isobutylene in 1.75 ml of methanol and 77 mg of methanesulfonic acid was treated with 93 mg of 2-[[(4-methoxy-3,5-dimethyl-2-pyridyl)methyl]sulfinyl]-5-(trifluoromethyl)benzimidazole, whereupon the reaction mixture was stirred at room temperature for 10 minutes and then neutralized with sodium bicarbonate solution. The sodium bicarbonate solution was extracted several times with methylene chloride. The combined organic phases were dried over sodium sulfate and concentrated. The residue was crystallized from ether/n-hexane in a refrigerator. The intramolecularly deprotonized 4-methoxy-2-[[(2-methoxy-2-methylpropyl)thio]methyl-1-[5-(trifluoromethyl)-2-benzimidazolyl]pyridinium cation obtained exhibited a melting point of 90°–93° (decomposition).

EXAMPLE 31

A solution of 5 ml of cyclohexene and 1 g of methanesulfonic acid in 20 ml of methanol was treated with 2 g of 2-[[(4-methoxy-3-methyl-2-pyridyl)methyl]sulfinyl]-5 (trifluoromethyl)benzimidazole, whereupon the reaction mixture was stirred at room temperature for 24 hours and then neutralized with a sodium bicarbonate solution. The sodium bicarbonate solution was extracted several times with methylene chloride. The combined organic phases were dried over sodium sulfate and concentrated. The residue was crystallized from ether/n-hexane. The intramolecularly deprotonized 4-methoxy-2-[[(trans 2-methoxycyclohexyl)thio]methyl]-3-methyl-1-[5-(trifluoromethyl)-2-benzimidazolyl]pyridinium cation obtained exhibited a melting point of 115°–120° (decomposition).

EXAMPLE 32

450 mg of intramolecularly deprotonized 2-[((2-ethoxy-2-methylpropyl)thio]methyl]-4-methoxy-3-methyl-1-[5-(trifluoromethyl)-2-benzimidazolyl]-pyridinium cation were dissolved in methanol and treated with 110 mg of methanesulfonic acid. The solution was concentrated several times while adding n-hexane each time. The residue was crystallized from tert. butyl methyl ether. The 2-[[(2-ethoxy-2-methylpropyl)-thio]methyl]-4-methoxy-3-methyl-1-[5-(trifluoromethyl)-2-benzimidazolyl]pyridinium methanesulfonate obtained exhibited a melting point of 49°–54°.

EXAMPLE 33

310 mg of intramolecularly deprotonized 2-[[(2-acetoxy-2-methylpropyl)thio}methyl}-4-methoxy 3 methyl-1-[5-(trifluoromethyl)-2-benzimidazolyl]-pyridinium cation were dissolved in methanol, whereupon the solution was acidified with 4.7N methanolic hydrochlorio acid and subsequently concentrated. Ethyl acetate was added to the residue, the mixture was concentrated, ethyl acetate was again added thereto and the mixture was again concentrated. Recrystallization was carried out from ether and there was obtained 2-[[(2-acetoxy-2-methylpropyl)thio]methyl]-4-methoxy-3-methyl-1-[5-(trifluoromethyl)-2-benzimidazolyl]-pyridinium chloride of melting point 116°–118°.

EXAMPLE 34

A suspension of 380 mg of 2-[[(4-methoxy-3,5-dimethyl-2-pyridyl)methyl]sulfinyl]-5-(trifluoromethyl)benzimidazole in a solution of 0.2 g of isobutylene in 3 ml of tert.-butanol was treated with 0.6 g of molecular sieve (Union Carbide, Type 3A) and with a solution of 0.5 g of gaseous hydrogen chloride in 3.7 ml of tert. butanol. The reaction mixture was stirred at room temperature for 50 minutes, subsequently poured into a mixture of ice and aqueous sodium bicarbonate solution and then methylene chloride was added thereto. The mixture was filtered and the filtrate was extracted with methylene chloride. The organic phase was dried and concentrated. The residue was dissolved in 10 ml of methylene chloride. whereupon 0.7 g of silica gel (particle size: 0.04–0.06 mm) was added thereto and the mixture was stirred at room temperature for one hour. The silica gel was filtered off and the filtrate was concentrated. The residue was chromatographed on silica gel with methylene chloride/methanol (20:1) as the elution agent, using the medium pressure flash chromatography method. By recrystallization from ether/n-hexane intramolecularly deprotonized 2-[[(2-chloro-2-methylpropyl)thio]methyl]-4-methoxy-3,5-dimethyl-1-[5-(trifluoromethyl)-2-benzimidazolyl]pyridinium cation of melting point 92°–93° was obtained.

EXAMPLE 35

A suspension of 100 mg of intramolecularly deprotonized 2-[[(2-chloro-2-methylpropyl)thio]methyl]-4-methoxy-3,5-dimethyl-1-[5-(trifluoromethyl)-2-benzimidazolyl]pyridinium cation in 2 ml of 1N aqueous hydrochloric acid was stirred at room temperature for 10 hours and then poured into a mixture of ice and aqueous sodium bicarbonate solution. The aqueous phase was washed several times with methylene chloride; the combined organic phases were dried and concentrated. The residue was chromatographed on silica gel with methylene chloride/methanol (10:1) as the elution agent, using the medium pressure flash chromatography method. The resinous reaction product was dried in a high vacuum. whereby intramolecularly deprotonized 2-[[(2-hydroxy-2-methylpropyl)thio]methyl]-4-methoxy-3,5-dimethyl-1-[5-(trifluoromethyl)-2-benzimidazolyl]pyridinium cation was obtained as a foam. The microanalysis showed the following values:

Empirical formula; $C_{21}H_{24}F_3N_3O_2S$; MW 439.50
Calc.: C 57.39% H 5.50% N 9.56% S 7.29%
Found: C 57.15% H 5.96% N 9.11% S 7.00%

EXAMPLE 36

(a) A solution of 9.4 g of 2-(chloromethyl)-3-methyl-4-nitropyridine and 10 g of 5-(trifluoromethyl)-2-benzimidazolethiol in 260 ml of abs. acetone was treated with 3 g of finely ground potassium carbonate and stirred at room temperature under argon for 18 hours. 180 ml of acetone were distilled off in a vacuum, whereupon the remaining portion of the reaction mixture was poured on to ice. The crystallized-out product was filtered off and dried at 35° in a drying oven By recrystallization from ethyl acetate/n-hexane there was obtained 2-[[(3-methyl-4-nitro 2-pyridyl)methyl]thio]-5-(trifluoromethyl)benzimidazole of melting point 192°-193°.

(b) 600 mg of sodium hydride dispersion (55-60% in oil) were dissolved in 50 ml of abs. ethanol under argon. 3.68 g of 2-[[(3-methyl-4-nitro-2-pyridyl)methyl]thio]-5-(trifluoromethyl)benzimidazole were added thereto and the solution was left to stir at 70° for 1 hour. The solution was neutralized with glacial acetic acid and the mixture was then evaporated in a vacuum. The residue was treated with aqueous sodium bicarbonate solution and methylene chloride. The organic phase was separated and the aqueous phase was extracted several times with methylene chloride. The combined organic phases were dried and concentrated The residue was chromatographed on silica gel with methylene chloride/methanol (9:1), using the medium pressure flash chromatography method, pressure was produced with nitrogen gas. There was obtained 2-[[(4-ethoxy-3-methyl-2-pyridyl)methyl]thio]-5-(trifluoromethyl)benzimidazole. After recrystallization from ethyl acetate/ether the product melts at 173°-177°.

(c) 2-[[(4-Ethoxy-3 methyl-2-pyridyl)methyl]thio]-5-(trifluoromethyl)benzimidazole was also prepared as follows:

A solution of 5 g of 2-(chloromethyl) 4-ethoxy-3-methylpyridine and 5 g of 5-(trifluoromethyl) 2 benzimidazolethiol in 130 ml of abs. acetone was treated with 5 g of finely ground potassium carbonate and stirred at room temperature under argon for 2 hours. 100 ml of acetone were distilled off in a vacuum, whereupon the remaining portion of the reaction mixture was poured onto ice The crystallized-out product was filtered off and dissolved in methylene chloride. The solution obtained was washed with water, dried and concentrated. The residue was chromatographed on silica gel while eluting using methylene chloride and methylene chloride/ethyl acetate (1:1), with the medium pressure flash chromatography method. 2-[[(4 ethoxy-3-methyl-2-pyridyl) methyl]thio]-5-(trifluoromethyl)benzimidazole which melts at 173°-177° was obtained after recrystallization from ethyl acetate/ether.

(d) A solution of 2.5 g of 2-[[(4-ethoxy-3-methyl-2-pyridyl)methyl]thio]-5-(trifluoromethyl)benzimidazole in 20 ml of chloroform was treated rapidly under argon at −40° with a solution of 1.5 g of m chloroperbenzoic acid in chloroform The solution was subsequently stirred for 10 minutes and extracted with 10 percent sodium carbonate solution. The chloroform solution was treated with 3 drops of triethylamine, dried and concentrated. The 2-[[(4-ethoxy-3-methyl-2-pyridyl)methyl]sulfinyl]-5-(trifluoromethyl)-2-benzimidazole obtained was processed directly.

(e) 80 ml of ethanol saturated with isobutylene were treated with 2.7 g of 2 (4-ethoxy 3 methyl-2-pyridyl) methyl]sulfinyl]-5-(trifluoromethyl)-2-benzimidazole and a solution of 1 g of methanesulfonic acid in 5 ml of ethanol was added thereto under an isobutylene atmosphere The solution was stirred at room temperature for 18 hours and then concentrated. The residue was treated with methylene chloride and aqueous sodium bicarbonate solution The organic phase was separated and the aqueous phase was washed with methylene chloride The combined organic phases were dried and concentrated. The residue was chromatographed on silica gel while eluting using methylene chloride/methanol (10:1). with the medium pressure flash chromatography method. The intramolecularly deprotonized 4-ethoxy-2-[[(2-ethoxy-2-methylpropyl)thio]methyl]-1-[5-(trifluoromethyl)-2-benzimidazolyl]-pyridinium cation obtained was acidified in ether with gaseous hydrogen chloride, whereupon the solution was concentrated and the residue was crystallized from ether. There was obtained 4-ethoxy-2-[[(2-ethoxy-2-methylpropyl)-thio]-methyl]-1-[5-(trifluoromethyl)-2-benzimidazolyl]-pyridinium chloride melting at 145°-147° with decomposition.

EXAMPLE 37

(a) A suspension of 13 g of 5,6-dichloro-2-benzimidazolethiol in 360 ml of alcohol was treated with 13 g of 2-chloromethyl-4-methoxy 3-methylpyridine hydrochloride. A solution of 4 g of sodium hydroxide in 170 ml of water was added dropwise thereto while cooling with ice. The mixture was left to boil at reflux overnight and then concentrated to about 1/3 of its volume in a vacuum. After the addition of 600 ml of water the crystals were filtered off and thereupon washed thoroughly with water and then with ether. There was obtained 5,6-dichloro-2-[[(4-methoxy-3-methyl-2-pyridyl)methyl]thio]benzimidazole of melting point 254°-256°.

(b) A solution of 1.0 g of 5,6-dichloro-2-[[(4-methoxy-3-methyl-2-pyridyl)methyl]thio]benzimidazole in 150 ml of methylene chloride and 30 ml of methanol was treated with 0.5 g of potassium carbonate. 0.6 g of m-chloroperbenzoic acid was added thereto at −30° while stirring, whereupon the solution was stirred for an additional 5 minutes and subsequently poured into a mixture of 20 ml of saturated sodium bicarbonate solution and 20 ml of water. The separated organic phase was dried over sodium sulfate, treated with 0.5 ml of triethylamine and evaporated in a vacuum. Crystallization from methylene chloride-methanol-ether yielded 5,6-dichloro-2-[[(4-methoxy-3-methyl-2-pyridyl)methyl]sulfinyl]benzimidazole of melting point 173°.

(c) A solution of 2 g of methanesulfonic acid in 200 ml of ethanol was saturated with isobutylene gas for 45 minutes then treated with 3.7 g of 5,6-dichloro-2-[[(4-methoxy-3-methyl-2-pyridyl)methyl]sulfinyl]benzimidazole, stirred room temperature overnight and subsequently evaporated in a vacuum. The residue was taken up in methylene chloride, whereupon the solution was extracted with 100 ml of saturated sodium bicarbonate solution, washed neutral with water, dried and concentrated in a vacuum. Crystallization of the residue from methylene chloride/ petroleum ether (low-boiling) yielded intramolecularly deprotonized 1-(5,6-dichloro-2-benzimidazolyl)-2-[[(2-ethoxy 2 methylpropyl)thio]methyl]-4-methoxy-3-methylpyridinium cation of melting point 141°–143°.

EXAMPLE 38

A solution of 3.7 g of 5,6-dichloro-2-[[(4-methoxy-3-methyl-2-pyridyl)methyl]sulfinyl]benzimidazole in 200 ml of tert.butanol was saturated with isobutylene gas for 45 minutes, then treated with a freshly prepared solution of 23 g of hydrogen chloride gas in 200 ml of tert-.butanol, stirred at room temperature for 48 hours and subsequently evaporated in a vacuum. The residue was taken up in methylene chloride, whereupon the solution was extracted with 100 ml of saturated sodium bicarbonate solution washed neutral with water, dried and concentrated in a vacuum. Crystallization of the residue from methylene chloride/petroleum ether (low-boiling) gave intramolecularly deprotonized 2-[[(2-chloro-2-methylpropyl)thio]methyl]-1-(5,6-dichloro-2-benzimidazolyl) 4-methoxy-3-methylpyridinium cation of melting point 136°–138°.

EXAMPLE 39

A suspension of 2.7 g of 2-[[(4-ethoxy-3-methyl-2-pyridyl)methyl]sulfinyl]-5-(trifluoromethyl)benzimidazole in a solution of 1.4 g of isobutylene in 21 ml of tert.butanol was treated with 2 g of molecular sieve (Union Carbide type 3A) and with a solution of 3.5 g of gaseous hydrogen chloride in 26 ml of tert.butanol. The reaction mixture was stirred at room temperature for 50 minutes and subsequently poured on to a mixture of ice and 200 ml of aqueous sodium bicarbonate solution, whereupon methylene chloride was added. The insoluble part of the mixture was filtered off over silica gel and the filtrate was extracted several times with methylene chloride The organic phases were combined, dried with sodium sulfate, filtered and concentrated. The residue was dissolved in 80 ml of methylene chloride, whereupon 5 g of silica gel (particle size: 0.04-0.06 mm) were added and the mixture was stirred at room temperature for one hour. The silica gel was filtered off, the filtrate was concentrated and the residue was crystallized from ether. The intramolecularly deprotonized 2-[[(2-chloro-2-methylpropyl)thio]methyl]-4-ethoxy-3-methyl-1-[5-(trifluoromethyl)-2-benzimidazolyl]-pyridinium cation obtained exhibited a melting point of 152° (decomposition).

EXAMPLE 40

A suspension of 1.5 g of intramolecularly deprotonized 2-[[(2-chloro-2-methylpropyl)thio]methyl]-4-ethoxy 3-methyl-1-[5-(trifluoromethyl)-2-benzimidazolyl]pyridinium cation in 3o ml of 1N aqueous hydrochloric acid was stirred at room temperature for 9 hours and then poured into a mixture of ice and aqueous sodium bicarbonate solution, whereupon the mixture was extracted several times with methylene chloride. The combined methylene chloride extracts were dried with sodium sulfate, filtered and concentrated. The residue was chromatographed on silica gel with methylene chloride/methanol (20:1) as the elution agent, using the medium pressure flash chromatography method. By crystallization from ether there was obtained intramolecularly deprotonized 2-[[(2-hydroxy-2-methylpropyl)-thio]methyl]-4-ethoxy-3-methyl-1-[5-(trifluoromethyl) 2-benzimidazolyl]pyridinium cation of melting point 162° (decomposition).

EXAMPLE 41

A solution of 1.3 g of intramolecularly deprotonized 2-[[(2-hydroxy-2-methylpropyl)thio]methyl]-4-ethoxy-3-methyl-1-[5-(trifluoromethyl)-2-benzimidazolyl]-pyridinium cation in 4.1 ml of acetic acid and 8.3 ml of acetic anhydride was treated with 8 drops of perchloric acid and stirred at room temperature for 5 hours. The reaction mixture was neutralized with saturated aqueous sodium carbonate solution, extracted several times with ether. The extracts were dried over sodium sulfate, and the ether was evaporated off. The residue was crystallized from ether/n-hexane, whereby there was obtained intramolecularly deprotonized 2-[[(2-acetoxy-2-methylpropyl)-thio]methyl]-4-ethoxy-3-methyl-1-[5-(trifluoro methyl)-2-benzimidazolyl]-pyridinium cation of melting point 108°–109° (decomposition).

EXAMPLE 42

A solution of 2 g of intramolecularly deprotonized 2-[[[2-(2-hydroxyethoxy)-2-methylpropyl]thio]methyl]-4-methoxy-3-methyl-1-[5-(trifluoromethyl) 2 benzimidazoly)]pyridinium cation in 6.2 ml of acetic acid and 12.5 ml of acetic anhydride was treated with 8 drops of perchloric acid and stirred at room temperature for 5 hours. The reaction mixture was neutralized with saturated aqueous sodium carbonate solution, extracted several times with methylene chloride. The extracts were dried over sodium sulfate, filtered and the methylene chloride was evaporated off. The residue was chromatographed on silica gel with methylene chloride/methanol (10:1) as the elution agent, using the medium pressure flash chromatography method. By crystallization from ether/n hexane there was obtained intramolecularly deprotonized 2- [[[2-(2-acetoxyethoxy)-2-methylpropyl]thio]methyl]-4-methoxy-3-methyl-1-[5-(trifluoromethyl)-2-benzimidazolyl]pyridinium cation of melting point 85°–89°.

EXAMPLE 43

A solution of 1.3 g of methanesulfonic acid and about 8 g of gaseous isobutylene in 100 ml of isopropanol was treated with 2.5 g of 2-[[(4-methoxy.3-methyl-2-pyridyl)methyl]sulfinyl]5-(trifluoromethyl)benzimidazole. whereupon the reaction mixture was stirred at room temperature under an isobutylene atmosphere for 66 hours and then evaporated. The residue was treated with methylene chloride and aqueous sodium bicarbonate solution, the methylene chloride phase was separated and the aqueous phase was extracted with methylene chloride The combined organic phases were dried and concentrated. The residue was chromatographed on silica gel with methylene chloride/methanol (20:1) as the elution agent, using the medium pressure flash chromatography method. The purified reaction product was dissolved in ethyl acetate and acidified with a solution of gaseous hydrochloric acid in ethanol, whereupon the solvent system was distilled off. The residue was crystallized from ethyl acetate/ether, whereby there was obtained 2-(2-isopropoxy-2-methylpropyl)-4-methoxy-3-methyl-1-[5-(trifluoromethyl)-2-benzimidazolyl]pyridinium chloride of melting point 123°–126°.

Example A

Crystalline compounds of formula I can be used as the active substance for the preparation of hard gelatin capsules, the content of which has the following composition per capsule:

| | |
|---|---|
| Active substance | 50.0 mg |
| Lactose powd. | 40.0 mg |
| Lactose cryst. | 130.0 mg |
| Maize starch white | 20.0 mg |
| Talc | 8.0 mg |
| Magnesium stearate | 2.0 mg |
| Fill weight per capsule | 250.0 mg |

The active substance and the adjuvants are mixed with one another and the mixture is filled into hard gelatin capsules of suitable size. If necessary, the capsules are subsequently provided with a gastric fluid-resistant coating of hydroxypropylmethylcellulose phthalate.

We claim:

1. A compound of formula

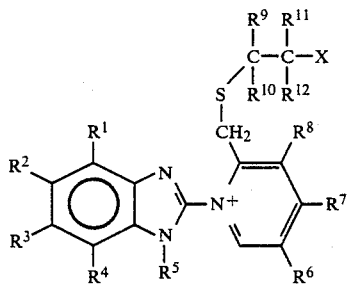

wherein
each of $R^1$, $R^2$, $R^3$ and $R^4$ independently is hydrogen, fluorine, chlorine, trifluoromethyl, cyano, a residue of the formula —COOR$^{13}$, —CONR$^{14}$R$^{15}$, —SOR$^{16}$ or —SO$_2$R$^{16}$
(a)     (b)     (c)     (d)

$R^5$ is hydrogen or a negative charge;
each of $R^6$ and $R^8$ are hydrogen or lower alkyl;
$R^7$ is lower alkoxy;
$R^9$ and $R^{10}$ each are hydrogen or lower alkyl;
$R^{11}$ and $R^{12}$ each are lower alkyl; or two of the substituents $R^9$ and $R^{10}$, or $R^9$ and $R^{11}$, or $R^{11}$ and $R^{12}$, taken together, are a divalent radical of the formula —(CH$_2$)$_4$— or —(CH$_2$)$_5$—, and the two remaining substituents of $R^9$, $R^{10}$, $R^{11}$ and $R^{12}$ each are hydrogen or lower alkyl; or $R^9$ and X together are an additional carbon-carbon bond, $R^{10}$ is hydrogen or lower alkyl and $R^{11}$ and $R^{12}$ each are lower alkyl;
$R^{13}$ is lower alkyl;
$R^{14}$ and $R^{15}$ each are hydrogen or lower alkyl or together with the nitrogen atom to which they are attached form a 5-, 6-, or 7-membered saturated heterocyclic ring;
$R^{16}$ is lower alkyl;
X is chlorine, bromine or -OR$^{17}$, or X and $R^9$ together are an additional carbon-carbon bond;
$R^{17}$ is hydrogen, a lower alkanoyl residue or —CH(R$^{18}$)R$^{19}$
(k)

wherein
$R^{18}$ is a hydrogen or lower alkyl; and
$R^{19}$ is hydrogen, lower alkyl, lower alkenyl, lower hydroxyalkyl, lower alkoxy-lower-alkyl, hydroxy-lower-alkoxy-lower-alkyl, lower alkoxy-lower-alkoxy-lower alkyl, hydroxy-lower-alkoxy-lower-alkoxy-lower alkyl, lower-alkoxy-lower-alkoxy-lower-alkoxy-lower-alkyl, lower-alkanoyloxy-lower alkyl or lower-alkanoyloxy-lower-alkoxy-lower-alkyl;
whereby the compound as a whole is non-charged or has a single positive charge and whereby in the letter case an external anion is present, 2. The compound of claim 1, wherein each of $R^1$, $R^2$, $R^3$ and $R^4$ is other than chlorine.

3. The compound of claim 1, wherein each of $R^1$ and $R^4$ are hydrogen; and each of $R^2$ and $R^3$ are fluorine or chlorine.

4. The compound of claim 1, wherein each of $R^1$ and $R^4$ are hydrogen; and $R^2$ is fluorine or trifluoromethyl and $R^3$ is hydrogen.

5. The compound of claim 4, wherein $R^2$ is trifluoromethyl and $R^3$ is hydrogen.

6. The compound of claim 1, wherein $R^6$ is hydrogen or methyl; $R^7$ is methoxy or ethoxy; and $R^8$ is methyl.

7. The compound of claim 6, wherein $R^7$ is methoxy.

8. The compound of claim 1, wherein each of $R^9$ and $R^{10}$ are hydrogen, each of $R^{11}$ and $R^{12}$ are methyl and X is chlorine, hydroxy, methoxy, ethoxy, propoxy, butoxy, acetoxy, 2-hydroxyethoxy, 2-methoxyethoxy, 2-(2-hydroxyethoxy)ethoxy, 2-(2-methoxyethoxy)ethoxy, 2-[2-(2-hydroxyethoxy)ethoxy]ethoxy or 2-[2-(2-methoxyethoxy)ethoxy]ethoxy.

9. The compound of claim 8, wherein each of $R^9$ and $R^{10}$ are hydrogen, each of $R^{11}$ and $R^{12}$ are methyl and X is chlorine, hydroxy, methoxy, ethoxy, propoxy, acetoxy, 2-hydroxyethoxy or 2-methoxyethoxy.

10. The compound of claim 9, wherein each of $R^9$ and $R^{10}$ are hydrogen, each of $R^{11}$ and $R^{12}$ are methyl and X is ethoxy, acetoxy, 2-hydroxyethoxy or 2-methoxyethoxy.

11. A compound of claim 1, wherein $R^9$ and X together form an additional carbon-carbon bond, $R^{10}$ is hydrogen and each of $R^{11}$ and $R^{12}$ are methyl, or $R^9$ and $R^{11}$ together are tetramethylene, each of $R^{10}$ and $R^{12}$ are hydrogen and X is methoxy.

12. The compound of claim 11, wherein $R^9$ and, X together form an additional carbon-carbon bond, $R^{10}$ is hydrogen and each of $R^{11}$ and $R^{12}$ are methyl.

13. The compound of claim 1 is 2-[[[2-(2-Hydroxyethoxy)-2-methylpropyl]thio]methyl]-4-methoxy-3-methyl-1-[5-(trifluoromethyl)-2-benzimidazolyl]pyridinium methanesulfonate.

14. The compound of claim 1 is intramolecularly deprotonized 2-[[[2-(2-hydroxyethoxy)-2 methylpropyl]thio]methyl]-4-methoxy-3-methyl-1-[5-(trifluoromethyl)-2-benzimidazolyl]pyridinium cation.

15. The compound of claim 1 is 4-Methoxy 2-[[[2-(2-methoxyethoxy)-2-methylpropyl]-thio]methyl]-3-methyl-1-[5-(trifluoromethyl)-2-benzimidazolyl]pyridinium methanesulfonate.

16. The compound of claim 1 is intramolecularly deprotonized 4-methoxy-2-[[[2-(2-methoxyethoxy)-2-methylpropyl]thio]methyl]-3-methyl-1-[5-(trifluoromethyl) 2-benzimidazolyl]pyridinium cation.

17. The compound of claim 1 is 2-[[(2-Acetoxy-2-methylpropyl)thio]methyl]-4-methoxy-3 methyl-1-[5-(trifluoromethyl)-2-benzimidazolyl]-pyridinium methanesulfonate.

18. The compound of claim 1 is 2-[[(2-Acetoxy-2methylpropyl)thio]methyl]-4-methoxy-3-methyl-1-[5-(trifluoromethyl)-2-benzimidazolyl]-pyridinium chloride 19. The compound of claim 1 is Intramolecularly deprotonized 2-[((2-acetoxy-2-methylpropyl) thio]methyl]-4-methoxy-3-methyl-1-[5-(trifluoromethyl)-2-benzimidazolyl]pyridinium cation.

20. The compound of claim 1 is 2-[[(2-Ethoxy2-methylpropyl)thio]methyl]-4-methoxy-3-methyl-1-[5-(trifluoromethyl)-2-benzimidazolyl]-pyridinium methanesulfonate.

21. The compound of claim 1 is 2-[(2-Ethoxy-2-methylpropyl)thio]methyl]-4-methoxy-3-methyl-1-[5-(trifluoromethyl)-2-benzimidazolyl]-pyridinium chloride.

22. The compound of claim 1 is intramolecularly deprotonized 2-[[(2-ethoxy-2-methylpropyl)thio]methyl]-4-methoxy-3-methyl-1-[5-(trifluoromethyl) 2-benzimidazolyl]pyridinium cation.

23. The compound of claim 1 selected from the group consisting of: intramolecularly deprotonized 2 [[(2-chloro-2-methylpropyl)thio]methyl]-4-methoxy-3-methyl-1-[5-(trifluoromethyl)-2-benzimidazolyl]-pyridinium cation; 2-[[(2-chloro-2-methylpropyl)thio]-methyl]-4-methoxy-3-methyl-1-[5-(trifluoromethyl)-2-benzimidazolyl]pyridinium chloride; intramolecularly deprotonized 2-[[(2-hydroxy-2-methylpropyl)methyl]-4-methoxy-3- methyl-1-[5-(trifluoromethyl)-2-benzimidazolyl pyridinium cation; intramolecularly deprotonized 4-methoxy-2-[[(2-methoxy-2-methylpropyl)-thio]methyl]-3-methyl-1-[5-(trifluoromethyl)-2-benzimidazolyl]pyridinium cation intramolecularly deprotonized 4-methoxy-3-methyl-2-[[(2-methyl-propenyl)thio]methyl]-1-[5-(trifluoromethyl)-2-benzimidazolyl]pyridinium cation; intramolecularly deprotonized 4-methoxy-3-methyl-2-[[(2-methyl-2-propoxypropyl)thio]methyl]-1-[5-(trifluoromethyl)-2-benzimidazolyl]pyridinium cation; 4-methoxy-3-methyl-2- [[(2-methylpropenyl)thio]methyl]-1-[5-(trifluoromethyl)-2-benzimidazolyl]pyridinium chloride; and intramolecularly deprotonized 2-[[(2-hydroxy-2-methylpropyl)thio]methyl]-4-methoxy-3,5-dimethyl-2-[5-(trifluoromethyl)-2- benzimidazolyl]pyridinium cation.

24. A anti-ulcer composition for treating or preventing gastric or duodenal ulcers comprising an effective amount of (a) a compound of formula

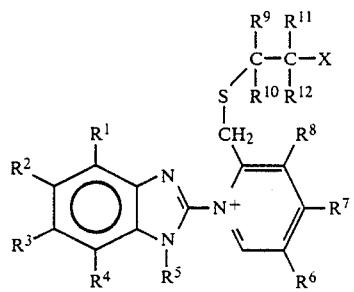

wherein
each of $R^1$, $R^2$, $R^3$ and $R^4$ independently is hydrogen, fluorine, chlorine, trifluoromethyl, cyano, a residue of the formula —COOR$^{13}$, —CONR$^{14}$R$^{15}$, —SOR$^{16}$ or —SO$_2$R$^{16}$
  (a)        (b)        (c)       (d)

$R^5$ is hydrogen or a negative charge;
each of $R^6$ and $R^8$ are hydrogen or lower alkyl;
$R^7$ is lower alkoxy;
$R^9$ and $R^{10}$ each are hydrogen or lower alkyl;
$R^{11}$ and $R^{12}$ each are lower alkyl; or two of the substituents $R^9$ and $R^{10}$, or $R^9$ and $R^{11}$, or $R^{11}$ and $R^{12}$, taken together, are a divalent radical of the formula -(CH$_2$)$_4$- or -(CH$_2$)$_5$-, and the two remaining substituents of $R^9$, $R^{10}$, $R^{11}$ and $R^{12}$ each are hydrogen or lower alkyl; or $R^9$ and X together are an additional carbon-carbon bond, $R^{10}$ is hydrogen or lower alkyl and $R^{11}$ and $R^{12}$ each are lower alkyl;
$R^{13}$ is lower alkyl;
$R^{14}$ and $R^{15}$ each are hydrogen or lower alkyl or together with the nitrogen atom to which they are attached form a 5-, 6- or 7-membered saturated heterocyclic ring;
$R^{16}$ is lower alkyl;
X is chlorine, bromine or -OH$^{17}$, or X and $R^9$ together are an additional carbon-carbon bond;
$R^{17}$ is hydrogen, a lower alkanoyl residue or —CH(R$^{18}$)R$^{19}$
(k)

wherein
$R^{18}$ is hydrogen or lower alkyl; and
$R^{19}$ is hydrogen, lower alkyl, lower alkenyl, lower hydroxyalkyl, lower alkoxy-lower-alkyl, hydroxy-lower-alkoxy-lower-alkyl, lower alkoxy-lower-alkoxy-lower alkyl, hydroxy-lower-alkoxy-lower-alkoxy-lower alkyl, lower-alkoxy lower-alkoxy-lower-alkoxy-lower-alkyl, hydroxy-lower-alkoxy-lower-alkoxy-lower-alkoxy-lower-alkyl, lower-alkanoyloxy-lower alkyl or lower-alkanoyloxy-lower-alkoxy-lower-alkyl
whereby the compound as a whole is non-charged or has a single positive charge and whereby in the latter case an external anion is present, said compound being present in a pharmaceutically effective amount; and (b) a pharmaceutically acceptable carrier.

25. A method of treating or preventing gastric or duodenal ulcers in a patient comprising administering an effective amount of a compound of formula

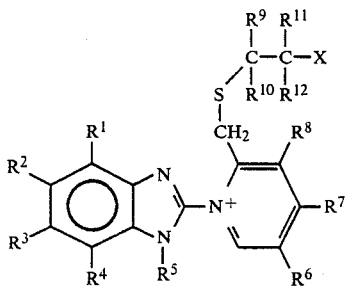

wherein
each of $R^1$, $R^2$, $R^3$ and $R^4$ independently is hydrogen, fluorine, chlorine, trifluoromethyl, cyano, a residue of the formula $$-COOR^{13}, -CONR^{14}R^{15}, -SOR^{16} \text{ or } -SO_2R^{16}$$
(a) (b) (c) (d)

$R^5$ is hydrogen or a negative charge;
each of $R^6$ and $R^8$ are hydrogen or lower alkyl;
$R^7$ is lower alkoxy;
$R^9$ and $R^{10}$ each are hydrogen or lower alkyl;
$R^{11}$ and $R^{12}$ each are lower alkyl; or two of the substituents $R^9$ and $R^{10}$, or $R^9$ and $R^{11}$, or $R^{11}$ and $R^{12}$, taken together, are a divalent radical of the formula —(CH$_2$)$_4$— or —(CH$_2$)$_5$—, and the two remaining substituents of $R^9$, $R^{10}$, $R^{11}$ and $R^{12}$ each are hydrogen or lower alkyl; or $R^9$ and X together are an additional carbon-carbon bond, $R^{10}$ is hydrogen or lower alkyl and $R^{11}$ and $R^{12}$ each are lower alkyl;

$R^{13}$ is lower alkyl;
$R^{14}$ and $R^{15}$ each are hydrogen or lower alkyl or together with the nitrogen atom to which they are attached form a 5-, 6- or 7-membered saturated heterocyclic ring;
$R^{16}$ is lower alkyl;
X is chlorine, bromine or —OR$^{17}$, or X and $R^9$ together are an additional carbon-carbon bond;
$R^{17}$ is hydrogen, a lower alkanoyl residue or $$-CH(R^{18})R^{19}$$
(k)

wherein
$R^{18}$ is hydrogen or lower alkyl; and
$R^{19}$ is hydrogen, lower alkyl, lower alkanoyl, lower hydroxyalkyl, lower alkoxy-lower-alkyl, hydroxy-lower-alkoxy-lower-alkyl, lower alkoxy-lower alkoxy-lower alkyl, hydroxy-lower-alkoxy-lower-alkoxy-lower alkyl, lower-alkoxy lower-alkoxy-lower-alkoxy-lower-alkyl, hydroxy-lower-alkoxy-lower-alkoxy-lower-alkoxy-lower-alkyl, lower-alkanoyloxy-lower alkyl or lower-alkanoyloxy-lower-alkoxy-lower-alkyl
whereby the compound as a whole is non-charged or bas a single positive charge and whereby in the latter case an external anion is present.

26. The method of claim 25 wherein said compound is orally administered to the patient in a daily dosage of about 30 to about 400 mg.

27. The method of claim 25 wherein said compound is intravenously administered to the patient in a daily dosage of about 30 to about 400 mg.

* * * * *

UNITED STATES PATENT AND TRADEMARK OFFICE
CERTIFICATE OF CORRECTION

PATENT NO. : 4,950,677

DATED : August 21, 1990

INVENTOR(S) : Albert Fischli, Anna Krasso and Andre Szente

It is certified that error appears in the above-identified patent and that said Letters Patent is hereby corrected as shown below:

In claim 1, column 26, line 16, after "-alkyl," and before "lower- alkanoyloxy-", add -- hydroxy-lower-alkoxy-lower-alkoxy-lower-alkoxy-lower-alkyl, --.

In claim 1, column 26, line 20, change "letter" to -- latter --.

In claim 23, column 27, line 43, after "methylpropyl)" and before "methyl]", insert -- thio] --.

In claim 23, column 27, line 61, after "dimethyl-" change "2" to -- 1 --.

In claim 25, column 30, line 16, change "alkanoyl" to -- alkenyl --.

In claim 25, column 30, line 27, change "bas" to -- has --.

Signed and Sealed this

Twenty-eighth Day of April, 1992

*Attest:*

HARRY F. MANBECK, JR.

*Attesting Officer*     *Commissioner of Patents and Trademarks*